(12) United States Patent
Yazaki et al.

(10) Patent No.: US 6,228,836 B1
(45) Date of Patent: May 8, 2001

US006228836B1

(54) PERMUCOUS PREPARATION

(75) Inventors: Takashi Yazaki; Mitsuo Hashimoto; Seiki Nakanishi, all of Tokyo (JP)

(73) Assignee: Mitsubishi-Tokyo Pharmaceuticals, Inc., Tokyo (JP)

( * ) Notice: Subject to any disclaimer, the term of this patent is extended or adjusted under 35 U.S.C. 154(b) by 0 days.

(21) Appl. No.: 09/402,886

(22) PCT Filed: Apr. 13, 1998

(86) PCT No.: PCT/JP98/01679

§ 371 Date: Oct. 18, 1998

§ 102(e) Date: Oct. 18, 1998

(87) PCT Pub. No.: WO98/46269

PCT Pub. Date: Oct. 22, 1998

(30) Foreign Application Priority Data

Apr. 14, 1997 (JP) .................................................. 9-095618

(51) Int. Cl.$^7$ .......................... A61K 47/26; A61K 37/02; A61K 47/00; C07K 7/16
(52) U.S. Cl. .............. 514/2; 530/315; 530/317; 530/328; 930/260; 424/422; 514/808; 514/807; 514/16
(58) Field of Search .................. 530/315, 317, 530/328, 316; 514/15, 16, 808, 807, 4, 2, 3, 800, 806, 19, 18, 17; 424/422, 180, 177, 16; 930/260; 260/112.5

(56) References Cited

U.S. PATENT DOCUMENTS

| | | | |
|---|---|---|---|
| 4,659,696 | 4/1987 | Hirai et al. | 514/15 |
| 4,670,419 | 6/1987 | Uda et al. | 514/16 |
| 4,690,952 | 9/1987 | Kagatani et al. | 514/808 |
| 4,788,221 | 11/1988 | Kagatani et al. | 514/808 |
| 5,211,950 | 5/1993 | Kobayashi et al. | 424/422 |
| 5,373,089 | 12/1994 | Flouret et al. | 530/315 |
| 5,929,027 | * 7/1999 | Takama et al. | 514/2 |

FOREIGN PATENT DOCUMENTS

| | | |
|---|---|---|
| 0 115 627 A1 | 8/1984 | (EP) . |
| 0308181 | * 3/1989 | (EP) ............................. A61K/47/00 |
| 0 308 181 A1 | 3/1989 | (EP) . |
| 59-130820 | 7/1984 | (JP) . |
| 61-267528 | 11/1986 | (JP) . |
| 62-185030 | 8/1987 | (JP) . |
| 63-2932 | 1/1988 | (JP) . |
| 63-39822 | 2/1988 | (JP) . |
| 63-196524 | 8/1988 | (JP) . |
| 2-214 | 1/1990 | (JP) . |
| 2-101020 | 4/1990 | (JP) . |
| 2-19092 | 4/1990 | (JP) . |
| 2-306921 | 12/1990 | (JP) . |
| 3-502920 | 7/1991 | (JP) . |
| 5-194260 | 8/1993 | (JP) . |
| 6-25068 | 4/1994 | (JP) . |
| 94/25485 | 11/1994 | (WO) . |

* cited by examiner

Primary Examiner—Christopher S. F. Low
Assistant Examiner—Patricia Robinson
(74) Attorney, Agent, or Firm—Nixon & Vanderhye

(57) ABSTRACT

A composition for permucosal administration characterized by containing Antago-3 or a physiologically acceptable salt thereof, and a sucrose fatty acid ester.

With the composition for permucosal administration of the invention there is provided a long-term stable preparation having the high permucosal absorption of physiologically active peptide Antago-3 without irritation.

5 Claims, No Drawings

PERMUCOUS PREPARATION

TECHNICAL FIELD

The present invention relates to a composition containing a compound represented by the following formula:

```
          1   2   3   4   5   6   7   8   9
        (S)Pmp-D-Trp-Ile-Gln-Asn-Pen-Pro-Arg-Gly-NH
           |                   |            (Antago-3)
           S-------------------S
```

Pmp: β,β-(3-thiapentamethylene)-p-mercaptopropionic acid
D-Trp: D-tryptophan
Pen: L-penicillamine
Ile: L-isoleucine
Asn: L-asparagine
Arg: L-arginine
Gln: L-glutamine
Pro: L-proline
(hereunder referred to as "Antago-3") or a physiologically acceptable salt thereof, and more specifically it relates to a permucosal preparation containing as an effective component Antago-3 or a physiologically acceptable salt thereof.

BACKGROUND ART

Antago-3 is a synthetic peptide with a molecular weight of 1172.47, which is an oxytocin analog with a powerful and specific oxytocin antagonism effect (WO94/25485-A).

Physiologically active peptides readily undergo enzymolysis by peroral or permucosal administration, while they are virtually unabsorbed by percutaneous administration due to their low membrane permeability, and hence they are generally administered in the form of injections.

For permucosal administration of physiologically active peptides, expression of their drug effects has required a method whereby an enzyme inhibitor or protective substance is added to protect the drugs from enzymes, or a method whereby an absorption enhancer is added to promote absorption of the drugs before their degradation.

As permucosal preparations of physiologically active peptides there are known preparations containing cyclodextrin (Japanese Patent Publication No. 19092 of 1990), preparations containing bile acid (Japanese Patent Publication No. 25068 of 1994, Japanese Laid-open Patent Publications No. 2932 of 1988 and No. 194260 of 1993), preparations containing surfactants (Japanese Laid-open Patent Publications No. 130820 of 1984 and No. 185030 of 1987), preparations containing absorption accelerators (Japanese Laid-open Patent Publications No. 267528 of 1986 and No. 196524 of 1988), preparations containing sucrose fatty acid esters (Japanese Laid-open Patent Publications No. 39822 of 1988, No. 214 of 1990 and No. 101020 of 1990), preparations containing saccharides (Japanese Laid-open Patent Publication No. 502920 of 1991) and preparations containing ethylenediamine tetraacetate (Japanese Laid-open Patent Publication No. 306921 of 1990), but no permucosal preparation is known that contains Antago-3 or a physiologically acceptable salt thereof as an effective component.

DISCLOSURE OF INVENTION

When an aqueous solution (10 μg/kg) of Antago-3 acetate (hereunder referred to simply as "Antago-3") was intravenously administered to rats, the response rate on uterine motility was 30% after 30 minutes, and the response rate was 5% after one hour.

However, with pernasal administration of the Antago-3 aqueous solution, it was not possible to express a similar drug effect with intravenous administration even at a dose of 400 μg/kg.

When polyoxyethylene polyoxypropylene ether, lecithin, sodium caprylate, sodium caprate, aprotinin or bacitracin, sodium ethylenediamine tetraacetate, sodium deoxycholate, β-cyclodextrin, sodium salicylate or disodium glycyrrhizinate was added to the Antago-3 aqueous solution as an absorption enhancer, it was not possible to express the drug effect obtained by intravenous administration with any of these other than sodium deoxycholate. Incidentally, sodium deoxycholate was shown to have an irritating effect on the nasal cavity mucosa.

The absorption enhancing effect of adding polysorbate 80, polyoxyethylene sorbitan monolaureate, taurine or N,N-dimethylacetamide (hereunder, "DMA") to the Antago-3 aqueous solution was evaluated based on the Antago-3 blood concentration and blood concentration area under the curve (hereunder, "AUC"), but no absorption enhancing effect was exhibited by any of the compounds.

For permucosal administration of an absorption enhancer-added Antago-3 liquid preparation, it is necessary that the presence of the additive cause no non-uniformity such as clouding or precipitation, or irritation at the site of administration.

The present inventors have conducted diligent research on permucosal preparations containing Antago-3 as the effective component, and as a result we have found that when a composition containing Antago-3 and a sucrose fatty acid ester (hereunder referred to a "composition of the invention") is administered, the Antago-3 is very efficiently absorbed through the nasal mucosa and rectal mucosa, thus allowing expression of a drug effect.

However, it was not easy to maintain a transparent state for an aqueous preparation containing the composition of the invention, due to clouding or precipitation of the sucrose fatty acid ester.

Upon conducting diligent research on Antago-3-containing aqueous preparations that maintain transparency, the present inventors then found, surprisingly, that the preservative benzalkonium chloride (hereunder, "BZCL") has a preventive a effect against clouding and precipitation of the sucrose fatty acid ester while also causing virtually no mucosal irritation so that it is highly safe for the body, and the present invention has thus been completed.

The composition for permucosal administration provided by the invention comprises a sucrose fatty acid ester in a proportion of 0.25–50 parts by weight to one part by weight of Antago-3. The fatty acid of the sucrose fatty acid ester may be stearic acid, palmitic acid, myristic acid, lauric acid, etc., and esters, diesters and triesters of these fatty acids, or mixtures thereof, may be used.

The preparation form may be a solution preparation or other type of liquid preparation, or a powder preparation.

BZCL may be used as a preservative that can be added to the aqueous preparation as a solution preparation, and it is combined at 0.03–0.5 part by weight, and preferably 0.04–0.16 part by weight of BZCL to one part by weight of the sucrose fattyacidester. Asisotonizingagentstheremaybementioned polyols such as glycerin and propylene glycol, saccharides such as mannitol, and nicotinamide, and as viscosity agents there may be mentioned hydroxypropylcellulose (hereunder, "HPC"), polyvinylpyrrolidone (hereunder, "PVP"), carboxymethylcellulose sodium (hereunder, "CMC-Na") and polyvinyl alcohol (hereunder, "PVA").

A powder preparation may be administered by a method whereby a mixture of the composition of the invention with lactose, sucrose, mannitol, sorbitol, crystalline cellulose, starch or a low-substituted HPC is sprayed by air power, or a method of spraying with an appropriate volatile carrier.

After adding the preservative, viscosity agent, surfactant, etc. to the composition of the invention, it may be filled into a container and used as a rectal preparation or vaginal preparation. As preservatives there may be mentioned p-hydroxybenzoic acid ester, BZCL, chlorobutanol and sodium dehydroacetate, as viscosity agents, HPC, PVP, CMC-Na, PVA and carboxyvinyl polymer, and as surfactants, hydrogenated castor oil and macrogol.

BEST MODE FOR CARRYING OUT THE INVENTION

The present invention will now be described by way of production examples. These examples, however, are not intended to be restrictive on the invention.

COMPARATIVE EXAMPLE 1

Antago-3 (10.0 mg) was dissolved in 100 mL of distilled water to make a 0.01% Antago-3 aqueous preparation.

COMPARATIVE EXAMPLES 2–4

According to the method of Comparative Example 1 there were prepared 0.4% Antago-3 (Comparative Example 2), 0.2% Antago-3 (Comparative Example 3) and 0.04% Antago-3 (Comparative Example 4) aqueous preparations.

COMPARATIVE EXAMPLE 5

A 1 mL aqueous solution of 0.16% Antago-3 and a 1 mL aqueous solution of 1.0% polyoxyethylene polyoxypropylene ether were thoroughly mixed to make a 0.08% Antago-3 aqueous preparation containing 0.5% polyoxyethylene polyoxypropylene ether.

COMPARATIVE EXAMPLES 6–20

According to the method of Comparative Example 5 there were made 0.08% Antago-3 aqueous preparations containing 0.5% lecithin (Comparative Example 6), 0.5% sodium caprylate (Comparative Example 7), 0.5% sodium caprate (Comparative Example 8), 0.1% aprotinin (Comparative Example 9), 0.1% bacitracin (Comparative Example 10), 1.0% sodium ethylenediamine tetraacetate (Comparative Example 11) and 1.0% sodium deoxycholate (Comparative Example 12), a 0.04% Antago-3 aqueous preparation containing 0.5% sodium deoxycholate (Comparative Example 13), and 0.08% Antago-3 aqueous preparations containing 0.5% β-cyclodextrin (Comparative Example 14), 0.1% sodium salicylate (Comparative Example 15), 1.0% disodium glycyrrhizinate (Comparative Example 16), 0.5% polysorbate 80 (Comparative Example 17), 0.5% polyoxyethylene sorbitan monolaurate (Comparative Example 18), 1.0% taurine (Comparative Example 19) and 3.0% DMA (Comparative Example 20).

COMPARATIVE EXAMPLE 21

After thoroughly mixing 1 mL of a 1.0% Antago-3 aqueous solution and 1 mL of a 1.0% sucrose fatty acid ester (stearic acid ester) solution, the mixture was lyophilized to obtain an Antago-3/sucrose fatty acid ester (1/1) composition for permucosal administration. To this there were added to dissolution 1 mL of a 5.0% glycerin aqueous solution and 1 mL of a 1.0% benzyl alcohol aqueous solution, to make an aqueous preparation of the composition for permucosal administration.

COMPARATIVE EXAMPLE 22

The Antago-3/sucrose fatty acid ester (1/1) lyophilized composition for permucosal administration of Comparative Example 21 was dissolved in an aqueous solution prepared by adding distilled water to 1 mL of a 5.0% glycerin aqueous solution, 0.2 mL of a 0.2% methylparaben aqueous solution and 0.2 mL of a 0.4% propylparaben aqueous solution, for a total of 2 mL, to make an aqueous preparation of the composition for permucosal administration.

COMPARATIVE EXAMPLE 23

Distilled water was added to 1 mL of a 5.0% Antago-3 aqueous solution and 1 mL of a 1.0% sucrose fatty acid ester (stearic acid ester) to a volume of 10 mL, to make an aqueous preparation of an Antago-3/sucrose fatty acid ester (1/0.2) composition for permucosal administration.

COMPARATIVE EXAMPLE 24

Distilled water was added to a mixture of 1 mL of a 0.8% Antago-3 aqueous solution, 5 mL of a 1.0% sucrose fatty acid ester (stearic acid ester) aqueous solution, 2 mL of a 12.5% glycerin aqueous solution and 0.25 mL of a 0.4% BZCL aqueous solution to a volume of 10 mL to make an aqueous preparation of an Antago-3/sucrose fatty acid ester (1/6.25) composition for permucosal administration.

EXAMPLE 1

After thoroughly mixing 1 mL of a 0.16% Antago-3 aqueous solution and 1 mL of a 1.0% sucrose fatty acid ester (stearic acid ester) aqueous solution, the mixture was lyophilized to obtain an Antago-3/sucrose fatty acid ester (1/6.25) composition for permucosal administration.

This was dissolved in 2 mL of distilled water to make an aqueous preparation of the composition for permucosal administration.

EXAMPLE 2

After thoroughly mixing 1 mL of a 0.08% Antago-3 aqueous solution and 1 mL of a 1.0% sucrose fatty acid ester (palmitic acid ester) aqueous solution and lyophilizing the mixture, the resulting Antago-3/sucrose fatty acid ester (1/12.5) composition for permucosal administration was dissolved in 2 mL of distilled water to make an aqueous preparation of the composition for permucosal administration.

EXAMPLE 3

After thoroughly mixing 1 mL of a 0.04% Antago-3 aqueous solution and 1 mL of a 1.0% sucrose fatty acid ester (stearic acid ester and palmitic acid ester at weight ratio of 1:1) aqueous solution and lyophilizing the mixture, the resulting Antago-3/sucrose fatty acid ester (1/25) composition for permucosal administration was dissolved in 2 mL of distilled water to make an aqueous preparation of the composition for permucosal administration.

EXAMPLE 4

After thoroughly mixing 1 mL of a 0.04% Antago-3 aqueous solution and 1 mL of a 0.2% sucrose fatty acid ester (stearic acid ester) aqueous solution and lyophilizing the mixture, the resulting Antago-3/sucrose fatty acid ester (1/5) composition for permucosal administration was dissolved in 2 mL of distilled water to make an aqueous preparation of the composition for permucosal administration.

EXAMPLE 5

After thoroughly mixing 1 mL of a 0.02% Antago-3 aqueous solution and 1 mL of a 1.0% sucrose fatty acid ester (stearic acid ester) aqueous solution and lyophilizing the mixture, the resulting Antago-3/sucrose fatty acid ester (1/50) composition for permucosal administration was dissolved in 2 mL of distilled water to make an aqueous preparation of the composition for permucosal administration.

EXAMPLE 6

The same treatment was carried out except that the sucrose fatty acid ester (stearic acid ester) of Example 1 was replaced with another sucrose fatty acid ester (sucrose lauric acid ester), and the resulting Antago-3/sucrose fatty acid ester (1/6.25) composition for permucosal administration was dissolved in 2 mL of distilled water to make an aqueous preparation of the composition for permucosal administration.

EXAMPLE 7

The Antago-3/sucrose fatty acid ester (1/6.25) composition for permucosal administration of Example 1 was dissolved in an aqueous solution prepared by adding distilled water to a mixed solution of 1 mL of a 5.0% nicotinamide solution and 0.2 mL of a 0.2% BZCL solution to a volume of 2 mL, to make an aqueous preparation of the composition for permucosal administration.

EXAMPLE 8

The Antago-3/sucrose fatty acid ester (1/6.25) composition for permucosal administration of Example 1 was dissolved in an aqueous solution prepared by adding distilled water to a mixed solution of 1 mL of a 10.0% sorbitol aqueous solution and 0.2 mL of a 0.2% BZCL solution to a volume of 2 mL, to make an aqueous preparation of the composition for permucosal administration.

EXAMPLE 9

The Antago-3/sucrose fatty acid ester (1/6.25) composition for permucosal administration of Example 1 was dissolved in an aqueous solution prepared by adding distilled water to a mixed solution of 1 mL of a 5.0% glycerin aqueous solution and 0.2 mL of a 0.2% BZCL solution to a volume of 2 mL, to make an aqueous preparation of the composition for permucosal administration.

EXAMPLE 10

Distilled water was added to 1 mL of a 0.8% Antago-3 aqueous solution, 1 mL of a 5% sucrose fatty acid ester (stearic acid ester) aqueous solution, 2 mL of a 12.5% glycerin aqueous solution, 1 mL of a 0.1% methylparaben-0.2% propylparabenmixed aqueous solution, 3 mL of a 10% HPC aqueous solution and 1 mL of a 0.2% BZCL aqueous solution to a volume of 10 mL to make an aqueous preparation of an Antago-3/sucrose fatty acid ester (1/6.25) composition for permucosal administration.

EXAMPLE 11

Distilled water was added to 1 mL of a 0.8% Antago-3 aqueous solution, 1 mL of a 5% sucrose fatty acid ester (stearic acid ester) aqueous solution, 2 mL of a 12.5% glycerin aqueous solution, 1 mL of a 5% benzyl alcohol aqueous solution, 3 mL of a 10% HPC aqueous solution and 1 mL of a 0.2% BZCL aqueous solution to a volume of 10 mL to make an aqueous preparation of a composition for permucosal administration.

EXAMPLE 12

After adding 10 mL of a 1.0% sucrose fatty acid ester (stearic acid ester) solution, 9.2 g of 2% Hibis Waco 105 (trade name: Wako Junyaku) as a gel base and a 1 mol/L sodium hydroxide aqueous solution (0.8 g) to Antago-3 (16.0 mg), the total was brought to 20 g with distilled water and thoroughly mixed to make a gel preparation of an Antago-3/sucrose fatty acid ester (1/6.25) composition for permucosal administration.

EXAMPLE 13

Distilled water was added to 1 mL of a 5.0% Antago-3 aqueous solution, 5 mL of a 1.0% sucrose fatty acid ester (stearic acid ester) aqueous solution, 2 mL of a 12.5% glycerin aqueous solution and 2 mL of a 0.4% BZCL aqueous solution to a volume of 10 mL to make an aqueous preparation of an Antago-3/sucrose fatty acid ester (1/i) composition for permucosal administration.

EXAMPLE 14

Distilled water was added to 1 mL of a 0.8% Antago-3 aqueous solution, 5 mL of a 1.0% sucrose fatty acid ester (stearic acid ester) aqueous solution, 2 mL of a 12.5% glycerin aqueous solution and 2 mL of a 0.4% BZCL aqueous solution to a volume of 10 mL to make an aqueous preparation of an Antago-3/sucrose fatty acid ester (1/6.25) composition for permucosal administration.

EXAMPLE 15

Distilled water was added to 1 mL of a 0.8% Antago-3 aqueous solution, 5 mL of a 1.0% sucrose fatty acid ester (stearic acid ester) aqueous solution, 2 mL of a 12.5% glycerin aqueous solution and 1 mL of a 0.4% BZCL aqueous solution to a volume of 10 mL to make an aqueous preparation of an Antago-3/sucrose fatty acid ester (1/6.25) composition for permucosal administration.

EXAMPLE 16

An aqueous preparation of a composition for permucosal administration was made by the same procedure in Example 15 except that the 0.4% BZCL aqueous solution was replaced with a 0.2% BZCL aqueous solution.

EXAMPLE 17

Distilled water was added to 1 mL of a 5.0% Antago-3 aqueous solution, 2 mL of a 2.0% sucrose fatty acid ester (stearic acid ester) aqueous solution, 2 mL of a 12.5% glycerin aqueous solution and 1 mL of a 0.2% BZCL aqueous solution to a volume of 10 mL to make an aqueous preparation of an Antago-3/sucrose fatty acid ester (1/0.8) composition for permucosal administration.

EXAMPLE 18

Preparation 1 for Monkey

Distilled water was added to 50 mg of Antago-3, 4 mL of a 2.5% sucrose fatty acid ester (stearic acid ester) aqueous solution, 2 mL of a 0.4% BZCL aqueous solution and 2 mL of a 12.5% glycerin aqueous solution to a volume of 20 mL to make an aqueous preparation of anAntago-3/sucrose fatty acid ester (1/2) composition for permucosal administration.

EXAMPLE 19

Preparation 2 for Monkey

An aqueous preparation of an Antago-3/sucrose fatty acid ester (1/1) composition for permucosal administration was made by the same procedure in Example 18 except that 2 mL of the 2.5% sucrose fatty acid ester (stearic acid ester) aqueous solution was used.

EXAMPLE 20

Preparation 3 for Monkey

An aqueous preparation of an Antago-3/sucrose fatty acid ester (1/0.4) composition for permucosal administration was made by the same procedure in Example 18 except that 0.8 mL of the 2.5% sucrose fatty acid ester (stearic acid ester) aqueous solution was used.

EXAMPLE 21

Preparation 4 for Monkey

An aqueous preparation of an Antago-3/sucrose fatty acid ester (1/0.5) composition for permucosal administration was made by the same procedure in Example 18 except that 100 mg of Antago-3 was used and 2 mL of the 2.5% sucrose fatty acid ester (stearic acid ester) aqueous solution was used.

EXAMPLE 22

Preparation 5 for Monkey

An aqueous preparation of an Antago-3/sucrose fatty acid ester (1/0.25) composition for permucosal administration was made by the same procedure in Example 18 except that 200 mg of Antago-3 was used and 2 mL of the 2.5% sucrose fatty acid ester (stearic acid ester) aqueous solution was used.

EXAMPLE 23

A 10 mg portion of an Antago-3/sucrose fatty acid ester (1/1) lyophilized composition for permucosal administration produced according to Comparative Example 21 was thoroughly mixed with 290 mg of lactose. A hard capsule (#4) was filled with 30 mg of the mixture to make a powder preparation of the composition for permucosal administration.

EXAMPLE 24

A powder preparation of a composition for permucosal administration was made according to the same procedure as Example 23, except that the lactose was replaced with crystalline cellulose.

EXAMPLE 25

After adding 10 mL of a 1.0% sucrose fatty acid ester (palmiticacidester) solution, 9.2 g of 2% Hibis Waco105 (trade name: Wako Junyaku) as a gel base and a 1 mol/L sodium hydroxide aqueous solution (0.8 g) to Antago-3 (16.0 mg), the total was brought to 20 g with distilled water and thoroughly mixed to make a gel preparation of an Antago-3/sucrose fatty acid ester (1/6.25) composition for permucosal administration.

EXAMPLE 26

A gel preparation of an Antago-3/sucrose fatty acid ester (1/6.25) composition was made by the same procedure as Example 25, except that the sucrose fatty acid ester (palmitic acid ester) was replaced with another sucrose fatty acid ester (myristic acid ester).

[Uterine Motility Response Rate]

(Method)

Estrus was induced in female rats (8 weeks old) with estradiol prior to the experiment. With each rat under urethane anesthesia, a catheter was inserted into the uterine horn, and after injection of physiological saline it was connected to a low-pressure transducer. A distortion measurement amplifier was used to record a rectigraph of uterine motility. After continuous intravenous infusion of oxytocin (50 mU/kg/min) through the femoral vein and confirmation of a stabilized contraction waveform, the test sample was pernasally administered (100 $\mu$L/kg). The suppressing effect on uterine motility by Antago-3 was expressed by the response rate, where 100% was defined as the multiplier of the average contraction frequency and amplitude in 10 minutes for the contraction waveform with oxytocin alone prior to administration of the sample. A response rate on uterine motility closer to 0% indicates that a stronger effect of Antago-3 was exhibited.

(Results)

The response rates on uterine motility with pernasal administration of Antago-3 aqueous solutions and aqueous solutions of the compositions of the invention are shown in Table 1, with intravenous administration of Antago-3 used as a control.

TABLE 1

Response rates on uterine motility with pernasal administration

| Sample | | Dosage ($\mu$g/kg) | Response rate (%) Time (hr) | | | | |
|---|---|---|---|---|---|---|---|
| | | | 0.5 | 1.0 | 1.5 | 2.0 | |
| Comparative Example | 1 | 10 | 30 | 5 | — | — | (intravenous injection) |
| | 2 | 400 | 80 | 25 | 20 | 20 | |
| | 3 | 200 | 90 | 70 | 60 | 50 | |
| | 4 | 40 | 100 | 100 | 100 | 100 | |
| | 5 | 80 | 100 | 100 | 100 | 100 | |
| | 6 | 80 | 100 | 100 | — | 100 | |
| | 7 | 80 | 100 | 100 | — | 100 | |
| | 8 | 80 | 90 | 50 | — | 40 | |
| | 9 | 80 | 100 | 100 | 100 | 100 | |
| | 10 | 80 | 100 | 100 | 100 | 100 | |
| | 11 | 80 | 100 | 100 | 100 | 100 | |
| | 12 | 80 | 0 | 0 | 0 | 10 | |
| | 13 | 40 | 30 | 20 | 15 | 10 | |
| | 14 | 80 | 100 | 100 | 80 | 40 | |
| | 15 | 80 | 80 | 80 | 80 | 80 | |
| | 16 | 80 | 100 | 90 | 80 | 75 | |
| Example | 1 | 80 | 0 | 0 | 0 | 0 | |
| | 2 | 40 | 5 | 0 | 0 | 0 | |
| | 3 | 20 | 10 | 5 | 5 | 5 | |
| | 4 | 20 | 30 | 10 | 10 | 10 | |
| | 5 | 10 | 30 | 15 | 10 | 5 | |

With intravenous administration of the Antago-3 aqueous solution, uterine motility was inhibited with a dosage of 10 $\mu$g/kg. With pernasal administration of the Antago-3 aqueous solution, a dosage of at least 400 $\mu$g/kg was required to obtain the same drug effect as the intravenous administration.

The sucrose fatty acid esters had a notable effect of enhanced Antago-3 absorption, with the aqueous solutions of the composition of the invention exhibiting activity roughly equivalent to that observed with intravenous administration.

No absorption enhancing effect was exhibited and uterine motility could not be inhibited when polyoxyethylene polyoxypropylene ether, lecithin, sodium caprylate, sodium caprate, aprotinin, bacitracin, sodium ethylenediamine tetraacetate, β-cyclodextrin, sodium salicylate or disodium glycyrrhizinate was added to Antago-3 as an absorption enhancer. When sodium deoxycholate was added, an absorption enhancing effect equivalent to that of the composition of the invention was exhibited.

[Absorption Enhancement by Blood Concentration AUC Method]

(Method)

(1) Pernasal Administration

A 100 μL/kg dose of the test sample was administered into both nasal cavities of awake 9-week-old female rats on a 16-hour fast, and 0.2 mL of blood was taken from the cervical vein at 15 minutes, 30 minutes, 1 hour, 2 hours and 4 hours after administration. The blood was transferred to an opaque blood collecting tube, and an inhibitor (a solution prepared by dissolving 100, 000 KIU of aprotinin (product of Wako Junyaku) and 4 mg of bestatin (product of Sigma Co.) in 5 mL of distilled water at the time of use) in an amount of 1/20 the amount of blood was silently added along the wall of the collecting tube, after which the blood was held in ice water and within 1.5 hours was centrifuged (4° C., 1600×g, 15 minutes) to obtain the blood plasma which was stored at −80° C. until measurement. The Antago-3 in the plasma was measured by radioimmunoassay (RIA)

(2) Perrectal Administration

The anus was held open with tweezers and the test sample was injected at 100 μL/kg in solution form or 100 μg/kg in gel form using an injection tube or a pipette, after which the anus was closed off with an adhesive to prevent leakage of the test sample. Blood was taken and measured in the same manner as for the pernasal administration.

The blood concentration area under the curve (AUC) was determined by the trapezoid method, and the absorption enhancement was expressed as the ratio to the AUC for the sample of <Comparative Example 2> in which no absorption enhancer was added. The test sample wherein 80 μg/kg of Antago-3 was administered was evaluated based on the value of 5 times the calculated AUC value for comparison with Comparative Example 2 (400 μg/kg administration).

(Results)

The results are shown in Tables 2 and 3.

TABLE 2

Blood concentration, AUC and absorption enhancement (pernasal administration)

| Sample | | Blood concentration (ng/mL) Time (hr) | | | | | $AUC_{o \to 4\ hr}$ (ng.hr/mL) | Absorption enhancement |
|---|---|---|---|---|---|---|---|---|
| | | 0.25 | 0.5 | 1.0 | 2.0 | 4.0 | | |
| Comparative | 2 | 3 | 2 | 2 | 2 | 1 | 7 | 1 |
| Example | 17 | 1 | 0 | 0 | 0 | 0 | — | — |
| | 18 | 7 | 3 | 0 | 0 | 0 | 3 | 2 |
| | 19 | 1 | 0 | 0 | 0 | 0 | — | — |
| | 20 | 1 | 0 | 0 | 0 | 0 | — | — |

TABLE 2-continued

Blood concentration, AUC and absorption enhancement (pernasal administration)

| Sample | | Blood concentration (ng/mL) Time (hr) | | | | | $AUC_{o \to 4\ hr}$ (ng.hr/mL) | Absorption enhancement |
|---|---|---|---|---|---|---|---|---|
| | | 0.25 | 0.5 | 1.0 | 2.0 | 4.0 | | |
| Example | 1 | 60 | 30 | 15 | 5 | 1 | 46 | 33 |
| | 6 | 55 | 25 | 15 | 3 | 1 | 38 | 27 |
| | 7 | 65 | 35 | 17 | 5 | 1 | 51 | 36 |
| | 8 | 55 | 25 | 15 | 3 | 1 | 38 | 27 |
| | 9 | 60 | 35 | 15 | 3 | 1 | 44 | 31 |
| | 10 | 50 | 20 | 10 | 3 | 1 | 31 | 22 |
| | 11 | 55 | 30 | 15 | 5 | 1 | 45 | 32 |

TABLE 3

Blood concentration, AUC and absorption enhancement (perrectal administration)

| Sample | | Blood concentration (ng/mL) Time (hr) | | | | | $AUC_{o \to 4\ hr}$ (ng.hr/mL) | Absorption enhancement |
|---|---|---|---|---|---|---|---|---|
| | | 0.25 | 0.5 | 1.0 | 2.0 | 4.0 | | |
| Comparative | 2 | 22 | 15 | 9 | 5 | 2 | 27 | 1 |
| Example | 1 | 35 | 27 | 15 | 10 | 1 | 46 | 9 |
| Example | 12 | 42 | 27 | 13 | 5 | 1 | 39 | 7 |

The absorption enhancements of the aqueous preparations and gel preparations of compositions according to the invention were 22-fold to 36-fold with pernasal administration and 7-fold to 9-fold with perrectal administration, compared to those with no addition of an absorption enhancer.

[Stability of Solution Preparations]

(Method)

Each of the solution preparations (Examples 13–17) made from a composition of the invention was placed in a transparent stoppered glass test tube, and stored at 5° C. Appearance were evaluated by visually observing the solution state at 1000 lux under a white fluorescent lamp.

(Results)

The preparations in which benzyl alcohol (Comparative Example 21) and methylparaben/propylparaben (Comparative Example 22) were added as preservatives, the preparation in which no preservative was added (Comparative Example 23) and the preparation with low addition of BZCL (Comparative Example 24) exhibited clouding after 3 days of storage, due to precipitation of the sucrose fatty acid esters. However, the preparations of Examples 13–17, in which at least 0.04 part by weight of BZCL was added to one part by weight of the sucrose fatty acid ester, maintained a colorless, transparent state.

[Nasal Mucosa Irritation]

(Method)

Eight-week-old female rats were used, with five per group. The rats were administered 100 μL/kg of the test sample into the nasal cavities once a day, for 7 continuous days. On the 8th day the nasal cavities were extracted, and after dividing them into 3 parts from the nasal cavity opening to the deep end of the nasal cavity, they were fixed with formalin to prepare specimens. After 10–14 days of fixing, a histopathological examination was made of the state of the mucosa, exudation and any bleeding.

Mild irritation was judged when abnormalities were found in the nasal mucosa at sections near the nasal cavity opening, and moderate to severe irritation was judged when the sections where abnormalities were found were further to the deep end. Moderate or greater irritation was also judged when degeneration, ablation, exudation or bleeding was found on the nasal mucosa epithelium at sections near the nasal cavity opening.

As controls there were used physiological saline and commercially available desmopressin (Kyowa Hakko Kogyo, KK.)

(Results)

The results are shown in Table 4.

TABLE 4

Nasal cavity mucosa irritation

|  | Normal | Mild | Moderate | Severe |
|---|---|---|---|---|
| Physiological saline | 3 | 2 | 0 | 0 |
| Desmopressin | 5 | 0 | 0 | 0 |
| Comparative Example 13 | 1 | 2 | 2 | 0 |
| Example 21 | 4 | 1 | 0 | 0 |
| Example 1 | 5 | 0 | 0 | 0 |
| Example 2 | 5 | 0 | 0 | 0 |
| Example 4 | 5 | 0 | 0 | 0 |
| Example 15 | 4 | 1 | 0 | 0 |

In the [Comparative Example 13] group there were observed exudation in the nasal mucosa and beaker cell proliferation in the respiratory epithelium, and therefore moderate irritation was determined.

Beaker cell proliferation was found in the respiratory epithelium of one rat in each of the [Comparative Example 21] and [Example 15] groups, but it was milder than in the [physiological saline] group used as a control.

No irritation was found in the [Example 1] group, [Example 2] group, [Example 4] group or [desmopressin] group.

No dead animals were found in any of the groups, nor were any abnormal symptoms found.

[Monkey Absorption Test]

A female monkey with a body weight of 3 kg was strapped to a monkey chair without anesthesia and in a state of rest, and the head was held so that the external naris was directed straight downward. A fixed-dose atomizing spray apparatus (spray volume: 50 μL/puff) filled with the test solution was then held vertically upward, and after stabilizing the spray condition by test spraying 4 or 5 times, the tip (about 1 cm) was inserted into the right nasal cavity and sprayed once for 50 μL. After spraying, the external naris was pointed forward and the external naris which had received the agent was closed with a finger and held for about 10 seconds in order to prevent run-off of the administered test solution, after which the left nasal cavity was sprayed in the same manner. The animal had been fasting from the evening of the day prior to administration, and it was fed after completion of the blood sampling during the 24 hours after administration.

For blood sampling, 0.3mL of blood was taken from the femoral vein or anterior humeroradial lateral cutaneous vein at 5, 15 and 30 minutes, and 1 and 2 hours (total of 5 times) after administration for preparations 1, 3, 4 and 5, and at 5, 15 and 30 minutes, and 1, 2, 4, 8 and 24 hours (total of 8 times) after administration for preparation 2.

The sampled blood was processed in the same manner as for the pernasal administration to obtain blood plasma which was stored at −80° C. until measurement.

[Measurement of Blood Concentration]

In an Isolute C18 cartridge (manufactured by Uniflex Co.) there were added 0.2 mL–0.05 mL of blood plasma, 0.1 mL of an internal standard solution (70% methanol solution containing 0.04 ppm reserpine) and 0.5 mL of a 0.1 M phosphate buffer solution (pH 7.0) to adsorb the contaminants in the plasma, and the Antago-3 was eluted out with 2 mL of 1-acetic acid-containing methanol. The eluate was distilled under reduced pressure, and 0.2 mL of a methanol:1.0% acetic acid mixture (7:3) was added to and dissolved in the residue to prepare a test solution. Separately, a bulk agent for quantitation was treated in the same manner and used as a standard solution. The test solution and the standard solution were subjected to liquid chromatography to determine the blood concentration.

TABLE 5

Blood concentrations

| | Blood concentration (ng/mL) | | | | |
|---|---|---|---|---|---|
| | 5 min | 15 min | 30 min | 1 hour | 2 hours |
| Example 18 | 112 ±23 | 372 ±105 | 346 ±80 | 456 ±52 | 368 ±78 |
| Example 19 | 286 ±111 | 491 ±193 | 419 ±105 | 313 ±66 | 407 ±107 |
| Example 20 | 74 ±23 | 102 ±105 | 160 ±80 | 96 ±52 | 130 ±78 |
| Example 21 | 385 ±152 | 1161 ±245 | 2087 ±651 | 2252 ±592 | 2424 ±692 |
| Example 22 | 828 ±345 | 2118 ±992 | 4201 ±2039 | 2903 ±1128 | 2851 ±1446 |

Note: mean value ±S.E. (n = 4)

The aqueous preparations of compositions according to the invention exhibited average blood concentrations that increased as the sucrose fatty acid ester concentration was higher, from 0.1% (Example 20) to 0.25% (Example 19) to 0.5% (Example 18), with a constant bulk agent concentration, and therefore the absorption enhancing effect depended on the concentration of the sucrose fatty acid ester. For Example 19, the bioavailability was 33% as determined by the AUC obtained from the blood concentrations for 24 hours after administration.

The blood concentrations increased as the bulk agent concentration was higher, from 0.25% (Example 19) to 0.5% (Example 21) to 1.0% (Example 22), with a constant sucrose fatty acid ester concentration.

Industrial Applicability

As explained above, a composition for permucosal administration according to the present invention is characterized by containing the physiologically active peptide Antago-3 or a physiologically acceptable salt thereof, and a sucrose fatty acid ester, and it has the high permucosal absorption of Antago-3 without irritation, rendering it useful as a long-term stable preparation.

What is claimed is:

1. A permucosal preparation comprising compound I:

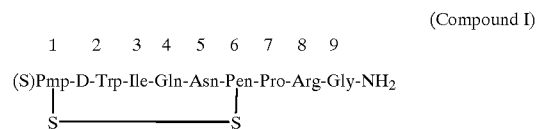

(Compound I)

Pmp: β,β-(3-thiapentamethylene)-β-mercaptopropionic acid,

D-Trp: D-tryptophan

Pen: L-penicillamine

Ile: L-isoleucine

Asn: L-asparagine

Arg: L-arginine

Gln: L-glutamine

Pro: L-proline or a physiologically acceptable salt thereof, a sucrose $C_{12}$–$C_{18}$ fatty acid ester, and benzalkonium chloride present in a proportion of 0.03 to 0.5 part by weight to one part by weight of the sucrose $C_{12}$–$C_{18}$ fatty acid ester.

2. A permucosal preparation according to claim 1, wherein the sucrose $C_{12}$–$C_{18}$ fatty acid ester is present in a proportion of 0.25–50 parts by weight to one part by weight of compound I or its physiologically acceptable salt.

3. A preparation according to claim 1 wherein the sucrose $C_{12}$–$C_{18}$ fatty acid ester is selected from the group consisting of a sucrose stearic acid ester, sucrose palmitic acid ester, sucrose myristic acid ester and sucrose lauric acid ester.

4. A preparation according to claim 1, which is suitable for per-nasal mucosa administration.

5. A permucosal preparation comprising compound I;

(Compound I)

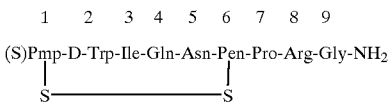

Pmp: β,β-(3-thiapentamethylene)-β-mercaptopropionic acid

D-Trp: D-tryptophan

Pen: L-penicillamine

Ile; L-isoleucine

Asn: L-asparagine

Arg: L-arginine

Gln; L-glutamine

Pro: L-proline or a physiologically acceptable salt thereof, a sucrose $C_{12}$–$C_{18}$ fatty acid ester, and benzalkonium chloride present in a proportion of 0.03 to 0.5 part by weight to one part by weight of the sucrose $C_{12}$–$C_{18}$ fatty acid ester, wherein the sucrose $C_{12}$–$C_{18}$ fatty acid ester is a mixture of one or more of sucrose stearic acid ester, sucrose palmitic acid ester, sucrose myristic acid ester or sucrose lauric acid ester.

* * * * *